United States Patent [19]

Agarwal

[11] Patent Number: 4,491,924
[45] Date of Patent: Jan. 1, 1985

[54] OLEFIN OXIDATION REACTOR TEMPERATURE CONTROL

[75] Inventor: Suresh C. Agarwal, Euclid, Ohio

[73] Assignee: The Babcock & Wilcox Company, New Orleans, La.

[21] Appl. No.: 375,795

[22] Filed: May 7, 1982

Related U.S. Application Data

[63] Continuation-in-part of Ser. No. 370,703, Apr. 22, 1982.

[51] Int. Cl.³ ............................................. G05D 7/100
[52] U.S. Cl. .................................. 364/500; 364/557; 422/62; 422/110
[58] Field of Search ............... 364/496, 500, 502, 557; 203/1; 436/55; 422/62, 105, 108, 110, 111; 260/700; 585/263, 401, 501, 950, 951

[56] References Cited

U.S. PATENT DOCUMENTS

| | | | |
|---|---|---|---|
| 3,271,472 | 9/1966 | Ogle et al. | 203/1 |
| 3,471,582 | 10/1969 | Lupfer | 436/55 |
| 4,111,218 | 9/1978 | Hobbs | 203/1 |
| 4,132,530 | 1/1979 | Schwimmer | 436/55 |
| 4,236,219 | 11/1980 | Killebrew, Jr. et al. | 422/66 |
| 4,241,230 | 12/1980 | Drinkard | 422/62 |
| 4,249,907 | 2/1981 | Callejas | 364/557 |
| 4,249,908 | 2/1981 | Funk | 364/557 |
| 4,329,150 | 5/1982 | Drinkard | 364/500 |

Primary Examiner—Raulfe B. Zache
Assistant Examiner—Dale M. Shaw
Attorney, Agent, or Firm—Vytas R. Matas; Robert J. Edwards

[57] ABSTRACT

A temperature control system controls the temperature of an olefin oxidation reactor by measuring various parameters in the reactor and in flow lines to and from the reactor, and using these parameters with known quantities for specific heat of the feed and effluent and heats of vaporization and reaction, to calculate a coolant flow rate set point. Parameters relating to the heat balance with regard to a desired olefin oxide product and undesired carbon dioxide products are utilized for correct control. Equipment is also provided for ascertaining the state of a catalyst used in the reaction. Circuit components are provided for obtaining changes in flow rates, temperatures and concentrations to calculate a change in coolant flow rate as well as the steady state fluent flow rate quantity to improve the system response to start up, shut down and transient conditions.

2 Claims, 2 Drawing Figures

OLEFIN OXIDATION REACTOR TEMPERATURE CONTROL

CROSS-REFERENCE TO RELATED APPLICATION

This is a continuation-in-part of a previous application entitled Temperature Control System for Olefin Oxidation Reactor filed Apr. 22, 1982 under Ser. No. 370,703 and presently co-pending.

FIELD AND BACKGROUND OF THE INVENTION

The present invention relates, in general, to temperature controlled equipment techniques in chemical reactors and, in particular, to a new and useful temperature control system for an olefin oxidation reactor which regulates the rate of coolant flow to maintain the reactor temperature within a desired temperature range, during the operation of the reactor as well as during start-up, shut-down and transient operating conditions.

Various techniques and systems are known for controlling chemical reactors.

In addition to the non-anticipating but relevant patents set forth in the parent application, U.S. Pat. No. 3,471,582 to Lupfer discloses an arrangement wherein a desired temperature across an exothermic reactor is maintained by controlling the reactor feed temperature in response to a difference in the temperature between the reactant feed and product stream from the reactor until a maximum predetermined product temperature is obtained.

U.S. Pat. No. 3,271,472 to Ogle et al discloses apparatus for controlling the operation of a thermal cracking furnace. Since the thermal cracking of hydrocarbons is an endothermic reaction, it is necessary to maintain a maximum possible temperature within the equipment limits. A minimum temperature is not considered or important in Ogle et al.

Also see U.S. Pat. No. 4,249,907 to Callegas which discloses a selective hydrogeneration process wherein at least one catalyst is utilized. The temperature of the feed steam to the catalyst bed is controlled so as to maintain a desired reaction temperature in the catalyst bed.

In an olefin, in particular ethylene, oxide manufacturing process, ethylene and oxygen or air is mixed and fet to an isothermal multitubular reactor. Ethylene is oxidized into ethylene oxide in the presence of a catalyst and carbon dioxide and water are produced as by-products. Reactor temperature control objectives are:
Operation at the most economical temperature;
Operation within a safe zone;
Maximum conversion to ethylene oxide while minimizing by-products;
Reduction consumption of coolant;
Avoidance or elimination of unsafe operation; and
Reduced operator attention.

Reactor temperature control is of key significance because of the following factors:

1. The most economical temperature for oxidation is one at which the highest conversion to ethylene oxide occurs rather than to by-products.
2. Catalyst selectivity increases as the reaction temperature is lowered while ethylene conversion increases with increasing reactor temperature. Thus, temperature requirements for high selectivity and high conversion are opposed. This results in a narrow temperature range for reactor operation.
3. Increase in reaction temperature produces two effects: (1) overall rate of ethylene oxidation increases, and (2) catalyst selectivity to ethylene oxide decreases such that relatively more ethylene is converted into carbon dioxide and water. Moreover, heat generation increases by the fact that more ethylene is oxidized and overall reaction becomes less selective. Consequently, increase in temperature may result in:
a reactor runaway condition;
catalyst poisoning;
increased coolant demand;
an unsafe operating situation; and/or
increased operator attention.

Hence, neither a temperature rise nor a temperature drop is desirable.

In the state of the art system, reactor temperature control system is based on manipulating coolant flow rate. Its set point is directly based upon average reactor temperature. These control schemes result in almost all the deficiencies described above.

SUMMARY OF THE INVENTION

An object of the present invention is to provide a control system and techniques which accomplishes the objectives of operating an olefin oxidation reactor at the most economical and safe temperature range, with regard to a maximum conversion of the olefin to the desired olefin oxide and a minimization of by-products.

Another object of the invention is to provide such a control system and technique, in particular for ethylene oxidation reactors.

Another object of the invention is to provide a control system and technique which is also applicable to other exothermic and endothermic reactors.

According to the invention, a system is provided which controls the rate of coolant flow in the chemical reactor according to an algorithm which incorporates various parameters including reactor feed and effluent flow rates, specific heat of reactants and products, reactor and effluent temperatures, coolant heat of evaporation, reactant and product concentration and heat of reactions for various reactions taking place in the reactor.

In addition, temperatures are taken at varied locations along the reactor length, for obtaining a maximum and a minimum value for temperatures within the reactor for establishing a desired reactor temperature range.

Accordingly, another objective of the invention is to provide a temperature control system and method for an olefin oxidation reactor which is simple in design, rugged in construction and economical to manufacture.

Another important feature of the invention is to provide an arrangement as set forth above for controlling the rate of coolant flow which, additionally, compensates for variations in operating conditions as well as provides proper coolant flow control even during start-up and shutdown phases of the operation.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
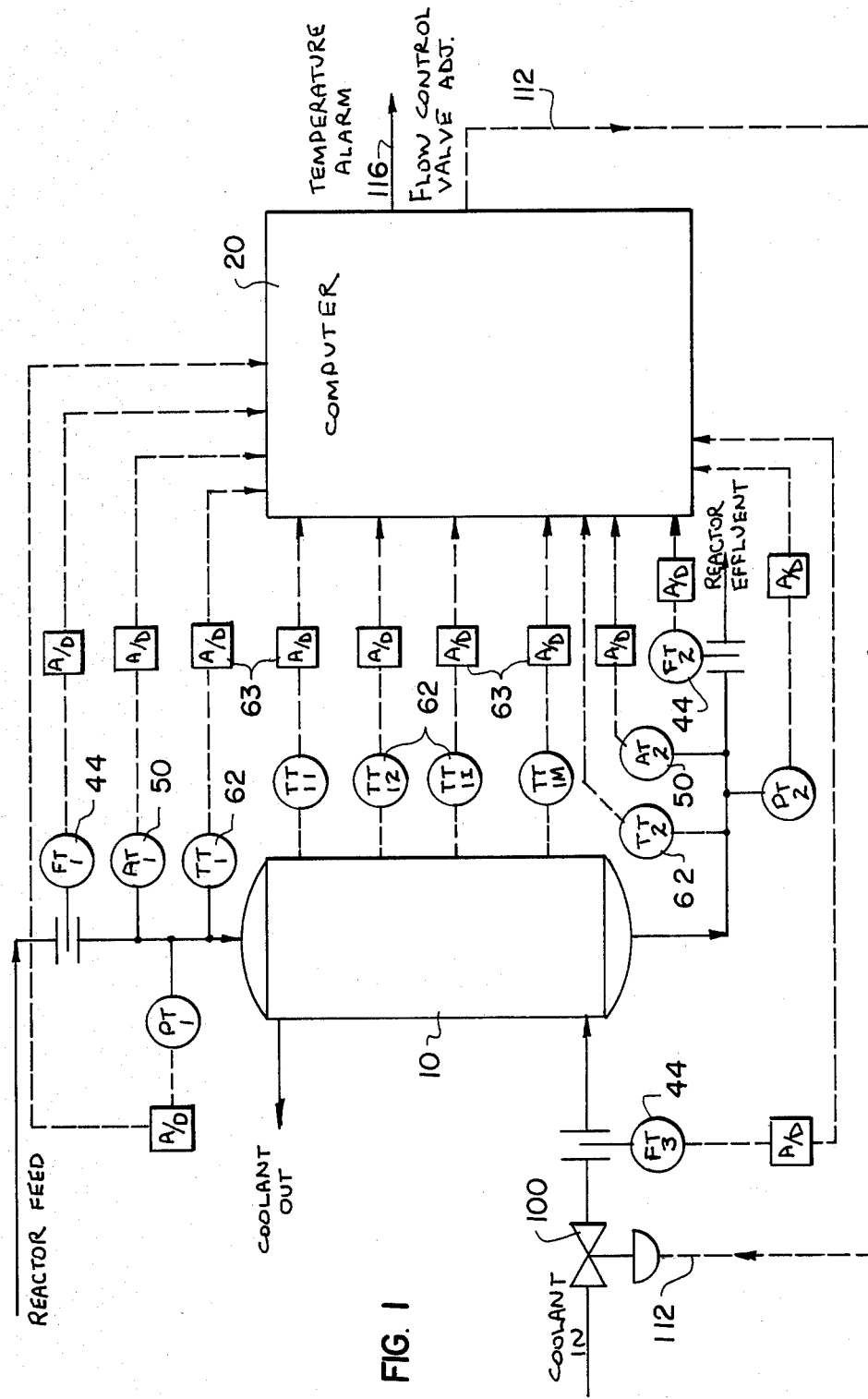
FIG. 1 is a schematic representation of the inventive control system in combination with a tubular reactor for containing an olefin oxidation reaction.

Referring to the drawings, in particular, the invention embodied therein in FIG. 1 comprises a control arrangement for controlling the flow of coolant into a tube reactor 10 by controlling the position of a valve 100 in a coolant inlet line. Controller valve 100 is achieved over line 112 connected to the output of a computer 20 which receives various inputs carrying signals corresponding to temperatures at various locations in the reactor and in the reactor feed and effluent lines and component concentrations. The computer is programmed with constants which relate to heats of various reactions going on in the reactor 10 and various physical characteristics of the coolant, the reactants and the products of the reaction.

The control system described in the parent application is based on the following assumptions:

a. Specific heat of reactor feed and effluent streams is assumed to be constant with changes in temperature and steam composition.
b. Heat of reaction is independent of temperature.

The above assumptions, however, while usually valid, do not hold during start-up, shut-down and transient reactor operating conditons. Consequently, coolant flow rate may be less than the desired rate, thus the reactor will operate at a temperature higher than necessary. The present control system takes these variations into account.

As shown in the parent application, coolant flow rate is given by the expression $$Q = \frac{1}{\lambda}[F_2\{y_1\Delta H_1 + y_2\Delta H_2 + C_{P1}(T_R - T_O)\} - F_1 C_{Pi}(T_R - T_I)] \quad (1)$$

where:
Q = Flow rate of coolant;
$\lambda$ = Heat of vaporization for coolant;
$F_1$ = Flow rate of feed;

$$C_{Pi} = \sum_{k=1}^{4} C_{Pk} X_k \text{ (for feed)}$$

$C_{PK}$ = specific heat of component k in feed; k=1 for ethylene, 2 for carbon dioxide, 3 for ethylene oxide and 4 for oxygen;
$X_k$ = Concentration of component $k$ in feed;
$T_R$ = Reaction temperature;
$T_I$ = Feed inlet temperature;
$T_O$ = Reactor Exit Stream temperature;

$$C_{P1} = \sum_{m=1}^{4} C_{pm} y_m \text{ (for effluent)}$$

$C_{Pm}$ = specific heat of component m in effluent; m=1 for ethylene oxide, m=2 for $CO_2$, m=3 for ethylene, m=4 for water;
$\Delta H_1$ = Heat of reaction for oxidation to ethylene oxide;
$\Delta H_2$ = Heat of reaction for oxidation to carbon dioxide and water;
$F_2$ = Flow rate of reactor effluent;
$y_1$ = a first produce (ethylene oxide) concentration; and
$y_2$ = a second produce ($CO_2$) concentration.

Functionally, equation (1) can be written as $$Q = f[F_1, F_2, T_I, T_R, T_O, y_1, y_2] \quad (2)$$

Then $$\frac{dQ}{dt} = \left[ \frac{\partial f}{\partial F_1}\frac{df_1}{dt} + \frac{\partial f}{\partial F_2}\frac{dF_2}{dt} + \frac{\partial f}{\partial T_I}\frac{dT_I}{dt} + \frac{\partial f}{\partial T_R}\frac{dT_R}{dt} + \frac{\partial f}{\partial T_O}\frac{dT_O}{dt} + \frac{\partial f}{\partial y_1}\frac{dy_1}{dt} + \frac{\partial f}{\partial y_2}\frac{dy_2}{dt} \right] \quad (3)$$

Since, dQ/dt is rate of change of Q with change in t, hence at fixed time intervals $$\Delta Q = Q(n) - Q(n-1) = \frac{dQ}{dt} \text{ for } t = T,$$

where T = control action interval.
Thus:

$$\Delta Q = \left[ \frac{\partial f}{\partial F_1}\Delta F_1 + \frac{\partial f}{\partial F_2}\Delta F_2 + \frac{\partial f}{\partial T_I}\Delta T_I + \frac{\partial f}{\partial T_R}\Delta T_R + \frac{\partial f}{\partial T_O}T_O + \frac{\partial f}{\partial y_1}\Delta y_1 + \frac{\partial f}{\partial y_2}\Delta y_2 \right] \quad (4)$$

where:

$$\frac{\partial f}{\partial F_1} = -[C_{Pi}(T_R - T_I)]/\lambda \quad (5)$$

$$\frac{\partial f}{\partial F_2} = [y_1\Delta H_1 + y_2\Delta H_2 + C_{P1}(T_R - T_O)]/\lambda \quad (6)$$

$$\frac{\partial f}{\partial T_I} = F_1 C_{Pi}/\lambda \quad (7)$$

$$\frac{\partial f}{\partial T_R} = (F_2 C_{P1} - F_1 C_i)/\lambda \quad (8)$$

$$\frac{\partial f}{\partial T_O} = -F_2 C_{P1}/\lambda \quad (9)$$

$$\frac{\partial f}{\partial y_1} = F_2\Delta H_1/\lambda \quad (10)$$

$$\frac{\partial f}{\partial y_2} = F_2\Delta H_2/\lambda \quad (11)$$

$$C_{Pi} = \sum_{k=1}^{4} C_{Pk} x_k \quad (12)$$

$$C_{P1} = \sum_{m=1}^{4} C_{pm} y_m \quad (13)$$

and, temperature dependence of specific heat and heat of reactions are given by;

$$\Delta H = \Delta H_O + \int^T C_p dT; \text{ and } C_p = a + bT + CT^2.$$

A control system according to the invention, can thus be obtained where all measured signals are interfaced to a control computer system by state of the art methods. A total control system is shown in Fig. 1.

Figure 2:
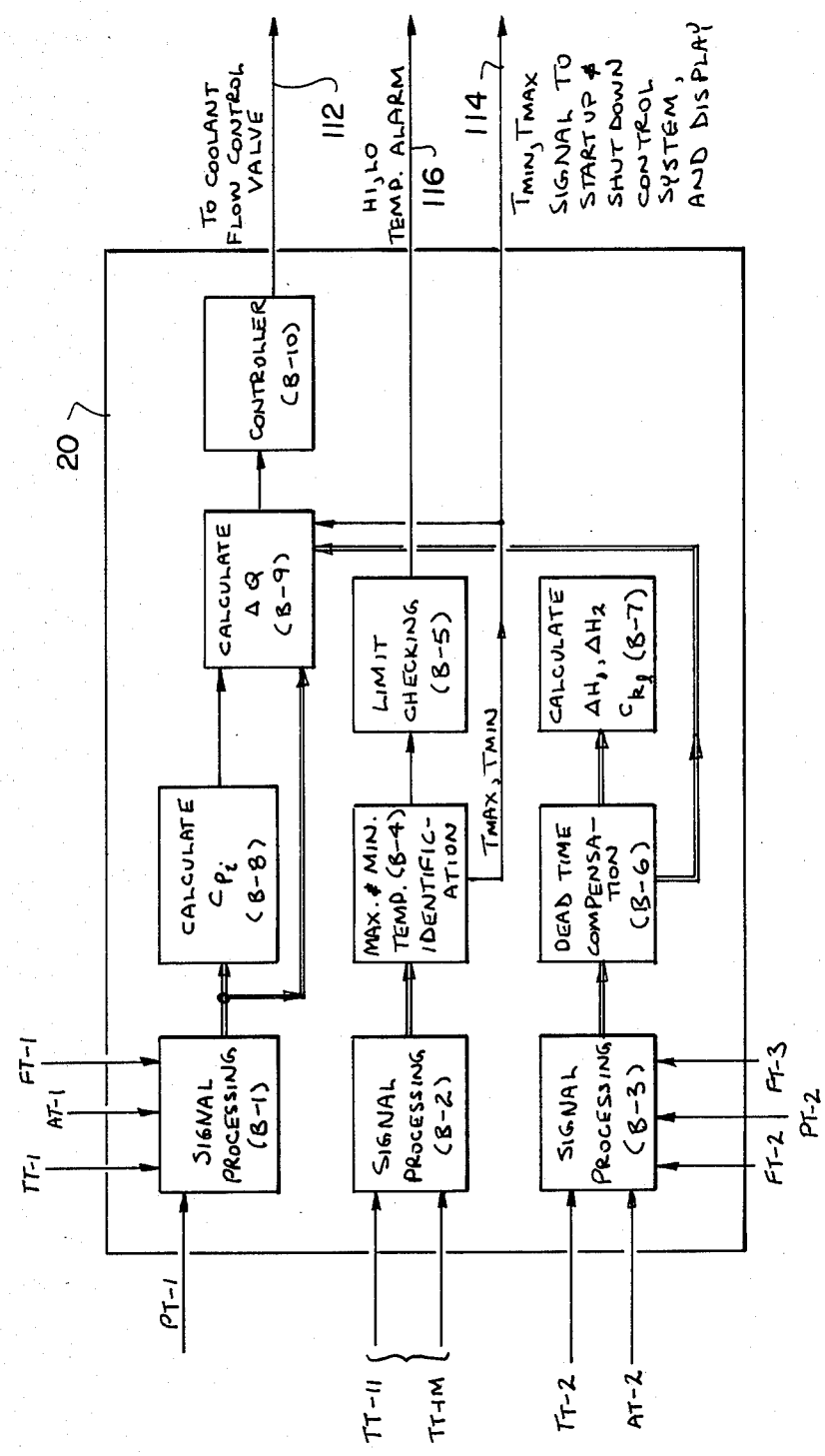
FIG. 2 is a block diagram which illustrates an exemplary computer layout for achieving the inventive purpose.

Major steps of the control system are given in FIG. 2. The calculations for block B-9 are those which have been developed above. Calculations in all other blocks are based upon commonly known practices.

The outputs are: coolant flow control valve setting at 112; minimum and maximum temperature signals to start-up and shut-down control systems (not shown here), and to display units at 114; and high low temperature alarms at 116. Other measured signals can be checked for high and/or low limits and alarmed as per need and operating practices of an individual reactor system.

While the implementation shown herein is through a control computer system, the invention can also be easily implemented by conventional electronic instrumentation and control systems.

Referring once more to the drawings, a plurality of temperature transmitters 62 provide temperature signals to computer 20 for the reactor feed line, the reactor 10 at various longitudinal locations thereof and the reactor effluent line. Each of the analog signals is converted in a corresponding analog to digital converter 63 into a corresponding digital signal which is readable by computer 20. In addition to the temperature transmitters, the invention is provided with a plurality of flow transmitters 44 and a plurality of concentration transmitters 50. Flow transmitters 44 provide analog signals which similarly are converted to corresponding digital signals corresponding to the reactor feed and effluent flow rate as well as the coolant flow rate. Concentration transmitters 50 provide signals corresponding to the concentration of various components in the feed and effluent line.

Each of the transmitters are further identified and correlated with inputs to the computer shown in FIG. 2. Temperature transmitters TT-11 through TT-1M provide their signals to a signal processing block B-2. The signals are then processed in a block B-4 to determine the maximum and minimum temperatures along the longitudinal length of the reactor. The signal is then supplied over line 14 to an output of computer 20 and also to a block B-9 for achieving calculations as pointed out above. Limit checking is accomplished in a block B-5 for sounding a low or high temperature alarm over line 116.

The transmitters and blocks identified above are all individually available in the art and will not described in greater detail.

According to the invention, thus, not only is the coolant flow rate Q as set forth in equation (1) obtained, but also the change in coolant flow rate $\Delta Q$. Equation (4) is utilized with each differential factor calculated as shown in equations (5) to equation (11). Simple comparators which relate an initial value with a later value can be utilized in computer 20 to obtain the values of flow rate change, $\Delta F_1$ and $\Delta F_2$, as well as the temperature and concentration change.

While a specific embodiment of the invention has been shown and described in detail to illustrate the application of the principles of the invention, it will be understood that the invention may be embodied otherwise without departing from such principles.

What is claimed is:

1. An arrangement for controlling the temperature of a reactor for containing a reaction from at least one reactant to at least another product, the reactor having a feed line for the reactant and an effluent line for the product, comprising:

a feed flow transmitter connected to the feed line for measuring the flow $F_1$ of reactant to the reactor;

an effluent flow transmitter connected to the effluent line for measuring the flow $F_2$ of product from the reactor;

a feed temperature transmitter connected to the feed line for sensing the reactant temperature $T_I$;

an effluent temperature transmitter connected to the effluent line for measuring the product temperature $T_O$;

at least one reactor temperature transmitter connected to the reactor for measuring a temperature of reactor $T_R$;

a concentration transmitter connected to the effluent line for measuring the concentration of the at least one product in the effluent line;

a coolant flow line to the reactor for supplying coolant to the reactor at a coolant flow rate;

coolant flow control means in said coolant line; and circuit means connected to all of said transmitters and to said coolant flow control means for controlling the flow of coolant to the reactor according to a coolant flow signal, said circuit means receiving quantities proportional to the heat of reaction for at least one reaction in the reactor, specific heats of the reactant and product, and the heat of vaporization of the coolant, said circuit means operable to obtain values for changes per unit time in feed flow rate $\Delta F_1$, effluent flow rate $\Delta F_2$, feed temperature $\Delta T_I$, reactor temperature, $\Delta T_R$, effluent temperature $\Delta T_O$, and concentration of at least one product $\Delta_y$, said circuit means including circuit components for multiplying each change per unit time by a characteristic factor said circuit means including circuit elements for generating factors as follows:

$$\frac{\partial f}{\partial F_1} = - [C_{P_i}(T_R - T_I)] / \lambda$$

$$\frac{\partial f}{\partial F_2} = [y_1 \Delta H_1 + y_2 \Delta H_2 + C_{P_1}(T_R - T_O)] / \lambda$$

$$\frac{\partial f}{\partial T_I} = F_1 C_{P_i} / \lambda$$

$$\frac{\partial f}{\partial T_R} = (F_2 C_{P_1} - F_1 C_i) / \lambda$$

$$\frac{\partial f}{\partial T_O} = -F_2 C_{P_1} / \lambda$$

$$\frac{\partial f}{\partial y_1} = F_2 \Delta H_1 / \lambda$$

$$\frac{\partial f}{\partial y_2} = F_2 \Delta H_2 / \lambda$$

said coolant flow signal being changed by a quantity $\Delta Q$ in said circuit means which is calculated as follows:

$$\Delta Q = \left[ \frac{\partial f}{\partial F_1} \Delta F_1 + \frac{\partial f}{\partial F_2} \Delta F_2 + \frac{\partial f}{\partial T_I} \Delta T_1 + \frac{\partial f}{\partial T_R} \Delta T_R + \frac{\partial f}{\partial T_O} T_O + \frac{\partial f}{\partial y_1} \Delta y_1 + \frac{\partial f}{\partial y_2} \Delta y_2 \right]$$

wherein:
- $\lambda$ = coolant heat of vaporization
- $y_1$ = a first product condensation
- $\Delta H_1$ = heat of reaction of reactant to first product
- $y_2$ = a second product concentration
- $\Delta H_2$ = heat of reaction of reactant to second product
- $C_{P_1}$ = specific heat of effluent, and wherein ethylene plus oxygen is supplied to the reactor as reactant and ethylene oxide plus carbon dioxide and water are generated as products, $y_1$ being the concentration of ethylene oxide, $y_2$ being the concentration of carbon dioxide, $\Delta H_1$ being the heat of reaction of ethylene plus oxygen to ethylene oxide, $\Delta H_2$ being the heat of reaction of ethylene plus oxygen to carbon dioxide.

2. An arrangement according to claim 1, wherein said reactor temperature sensing means comprises a plurality of temperature sensor distributed along the length of said reactor, and a minimizing/maximizing circuit connected to said temperature sensors for obtaining a minimum and a maximum temperature among said temperature sensors of the reactor.

* * * * *